United States Patent
Riechers

(10) Patent No.: US 9,809,793 B2
(45) Date of Patent: Nov. 7, 2017

(54) BIOREACTOR VESSEL HAVING AN OPTICAL FOAM SENSOR

(75) Inventor: Daniel Riechers, Hannover (DE)

(73) Assignee: SARTORIUS STEDIM BIOTECH GMBH, Goettingen (DE)

(*) Notice: Subject to any disclaimer, the term of this patent is extended or adjusted under 35 U.S.C. 154(b) by 0 days.

(21) Appl. No.: 13/521,230

(22) PCT Filed: Jan. 18, 2011

(86) PCT No.: PCT/EP2011/000186
§ 371 (c)(1),
(2), (4) Date: Jul. 10, 2012

(87) PCT Pub. No.: WO2011/098204
PCT Pub. Date: Aug. 18, 2011

(65) Prior Publication Data
US 2013/0039810 A1    Feb. 14, 2013

(30) Foreign Application Priority Data
Feb. 10, 2010 (DE) .................. 10 2010 007 559

(51) Int. Cl.
C12M 1/21    (2006.01)
C12M 1/00    (2006.01)

(52) U.S. Cl.
CPC ............ C12M 41/02 (2013.01); *C12M 23/14* (2013.01); *C12M 23/26* (2013.01)

(58) Field of Classification Search
CPC ....... C12M 29/20; C12M 23/14; C12M 23/26
(Continued)

(56) References Cited

U.S. PATENT DOCUMENTS 4,209,687 A * 6/1980 Bethge et al. ............... 219/522
5,476,573 A   12/1995 Hirose et al.
(Continued)

FOREIGN PATENT DOCUMENTS

DE    37 27 132    2/1989
DE    40 36 048    5/1991
(Continued)

OTHER PUBLICATIONS

DE3727132 machine translation (Feb. 1989).*
(Continued)

*Primary Examiner* — Jonathan M Hurst
(74) *Attorney, Agent, or Firm* — Gerald E. Hespos; Michael J. Porco; Matthew T. Hespos

(57) ABSTRACT

A bioreactor vessel has an optical foam sensor (36) with a foam contact surface for contacting the foam to be detected. The foam contact surface is an inner side of a window (38) transparent to light from the visible and ultraviolet spectral range in an outer wall of the bioreactor vessel (10). An outer side of the window (38) is coupled to an illumination and detection unit (52) with at least one first light source (56) of visible light and at least one photodetector (58) to detect light from the first light source (56) that is reflected in the bioreactor vessel (10). The foam contact surface has a titanium dioxide coating (44) superhydrophilizable by photoactivation with ultraviolet light and the illumination and detection unit (52) has at least one second light source (66) of ultraviolet light.

7 Claims, 1 Drawing Sheet

(58) Field of Classification Search
USPC ......... 435/283.1, 287.1, 286.1, 288.3, 288.7, 435/301.1, 808, 812
See application file for complete search history.

(56) References Cited

U.S. PATENT DOCUMENTS

| | | | |
|---|---|---|---|
| 5,597,950 | A | 1/1997 | Muller |
| 5,922,112 | A | 7/1999 | Zappi et al. |
| 6,207,110 | B1 | 3/2001 | Sullivan et al. |
| 2004/0253624 | A1* | 12/2004 | Smith et al. ............... 435/6 |
| 2005/0158701 | A1* | 7/2005 | West ................ C12M 41/48 435/286.1 |
| 2008/0068920 | A1* | 3/2008 | Galliher et al. ............ 366/102 |
| 2009/0075248 | A1* | 3/2009 | Debreczeny et al. ..... 435/288.7 |
| 2009/0075362 | A1* | 3/2009 | Baumfalk et al. ........ 435/289.1 |
| 2009/0130256 | A1 | 5/2009 | Uphoff |
| 2009/0135667 | A1* | 5/2009 | Terentiev ........... B01F 3/04248 366/142 |
| 2010/0022383 | A1 | 1/2010 | Kuntz et al. |
| 2010/0035337 | A1* | 2/2010 | Bahnemann et al. ..... 435/292.1 |

FOREIGN PATENT DOCUMENTS

| | | |
|---|---|---|
| DE | 41 42 967 | 7/1993 |
| DE | 203 03 829 | 8/2004 |
| DE | 10 2007 011 628 | 9/2007 |
| DE | 10 2006 038 249 | 2/2008 |
| DE | 10 2006 043 724 | 3/2008 |
| DE | 10 2006 044 076 | 3/2008 |
| EP | 1 004 338 | 5/2000 |
| EP | 1 950 281 | 9/2009 |
| JP | 2008-142604 | 6/2008 |
| WO | 00/11471 | 3/2000 |
| WO | 2007/131593 | 11/2007 |

OTHER PUBLICATIONS

EP 1950281 Petter machine translation (2008).*
International Preliminary Report on Patentability, (Aug. 23, 2012).

* cited by examiner

BIOREACTOR VESSEL HAVING AN OPTICAL FOAM SENSOR

BACKGROUND OF THE INVENTION

1. Field of the Invention

The invention relates to a bioreactor vessel having an optical foam sensor which comprises a foam contact surface for contacting the foam to be detected.

2. Description of the Related Art

More particularly, the invention relates to bioreactor vessels having flexible outer walls that are especially suitable for use as disposable bioreactor vessels.

EP 1 950 281 B1 discloses bioreactor vessels having optical foam sensors. However, the bioreactor vessels disclosed in the aforementioned document do not have flexible outer walls. Specific details about the optical foam sensors are not disclosed in the aforementioned document. However, what is disclosed is that the foam sensors have a contact surface which is composed of dirt- and water-repellent material and at which foam produced in the course of a reaction taking place in the bioreactor container comes into contact and can be detected. In many bioreactions, more particularly in cell cultures and fermentations, foam development is a virtually unavoidable, but undesired, process. In particular, there is the risk of foam blocking off-gas filters, and this can lead to a rise in pressure in the reactor. Especially in the case of bioreactor vessels having flexible outer walls, this can lead to leakages, which can only be prevented by automatically switching off the gas supply. However, this constitutes an adverse influence on the process in the reactor. It is possible to counter the phenomenon of foam development by the metered addition of surface-active substances, known as antifoaming agents. However, they can have an adverse effect on the possibly sensitive biological process in the reactor, and so they must be used very sparingly. This can only be achieved when the actual and current demand for antifoaming agents, i.e. the actual and current status of foam development, can be captured reliably and without a large time lag. Such capture must be achieved using reliable and fast foam detectors, which can be connected to controllable metering pumps for the antifoaming agents via appropriate control electronics.

The aforementioned document addresses the problem of foam permanently accumulating on the contact surface, so that the detector is not able to recognize foam regression brought about by metered-in antifoaming agents. This would lead to overmetering of the antifoaming agents with the abovementioned disadvantages. The corrective action proposed by the aforementioned document is for an interior space of the foam detector to be made so large that no capillary effect can develop which could retain the foam in the detector space. This is associated with a disadvantageous structural enlargement.

DE 10 2006 044 076 A1 discloses a photocatalytically active coating for surfaces of buildings, vehicles, appliances, equipment, pathways and the like which consists of titanium dioxide nanoparticles in the anatase configuration and is activated by the UV components of daylight.

It is an object of the present invention to provide a bioreactor vessel, more particularly a bioreactor vessel having flexible outer walls, which has improved foam sensor technology.

SUMMARY OF THE INVENTION

The invention relates to a bioreactor vessel having an optical foam sensor with a foam contact surface for contacting the foam to be detected. The foam contact surface is an inner side of a window transparent to light from the visible and ultraviolet spectral range in an outer wall of the bioreactor vessel and in that an outer side of the window is coupled to an illumination and detection unit comprising at least one first light source of visible light and at least one photodetector which makes it possible to detect light from the first light source that is reflected in the bioreactor vessel.

The present invention comprises a plurality of essential components. Firstly, there is no need for a separate foam detection space. Instead, the bioreactor vessel according to the invention is provided with a window in its outer wall, which window is a component of the foam sensor and, especially with its inner side, provides the foam contact surface. The arrangement of the window in the vessel outer wall depends in individual cases on the intended filling level of the vessel and on a foam level to be regarded as critical. The arrangement of a plurality of windows or foam detectors at, if necessary, different levels of the vessel is of course also possible. The term "outer wall of the bioreactor vessel" is also to be broadly understood and can also comprise connected lines.

Assigned to the window is an illumination and detection unit. This is coupled to the window from the outside. Preferably, the coupling is carried out reversibly, for example by means of a clip closure or a screw connection. This is advantageous especially in the case of disposable bioreactors, since the illumination and detection unit, which contains expensive and possibly difficult-to-sterilize electronics, can thus be designed to be reusable, whereas the window is a fixed component of the disposable vessel, and together therewith can be sterilized and disposed of after use.

The illumination and detection unit contains at least one first light source of visible light. This is advantageously in the form of an LED. The illumination and detection unit further contains at least one photodetector which is capable of detecting light from the spectral range emitted by the aforementioned LED. The first light source and photodetector are arranged relative to one another such that no light from the LED falls directly onto the photodetector. Instead, the LED radiates through the window into the interior space of the reactor vessel. If foam has formed in front of the window, it reflects the irradiated light. The reflected light is collected by the photodetector, which generates a corresponding reflection signal. If no foam is situated in front of the window, distinctly less light is reflected, and so the resulting reflection signal is distinctly lower. Appropriate determination of a threshold value to be performed in individual cases by a person skilled in the art allows a distinction to be made between "foam" and "no foam".

In a preferred embodiment, the inner side of the window, i.e. the foam contact surface, is coated with a UV-activatable, photocatalytic titanium dioxide coating. Here, it is preferably a nanocrystalline coating composed of titanium dioxide in the anatase configuration and/or rutile configuration that is known in principle, wherein an at least predominant proportion of anatase crystals is preferred. It is known that upon irradiation with UV light, more particularly with light having a wavelength of less than 390 nanometers, coatings of this kind exhibit two effects, which the invention utilizes in an advantageous manner. Firstly, so-called superhydrophilicity of the coated surface occurs. This means that the water contact angle is distinctly reduced, and so adherent droplets run and completely wet the surface. As a result, the formation of optically scattering drops of dew is prevented and flow-off from the surface is facilitated. As a second effect, electron-hole pairs are formed in the titanium dioxide.

This effect is based on the fact that the band gaps of the semiconductor material titanium dioxide can be overcome by UV irradiation. The electron-hole pairs migrate to the surface of the layer and react there with adsorbed oxygen or water to form hydroxyl radicals. These radicals, as highly reactive chemical species, are capable of attacking and breaking down organic dirt, and so organic dirt, i.e. foam in the present case, is actively destroyed by the photocatalysis. The end products of the completed photocatalytic reaction which are formed are carbon dioxide and water. The latter readily flows off on the superhydrophilic surface and washes the window completely clean.

For the specific activation of the photocatalytic layer, the illumination and detection unit contains a second light source, preferably also an LED, which emits ultraviolet light comprising at least components having a wavelength below 390 nanometers. The UV light source should of course be orientated such that it radiates through the window.

Further preferred embodiments of the present invention are subject matter of the dependent claims.

Preferably, the illumination and detection unit comprises a coupling surface in the form of a sealing plate transparent to light from the visible and ultraviolet spectral range. Said sealing plate preferably provides a liquid-tight seal for a housing in which the at least one first light source, the at least one second light source and the at least one photodetector are arranged. In this way, the illumination and detection unit forms a closed module which can be reused as often as desired and provides the sensitive electronics contained therein with sufficient protection even in a harsh environment. The sealing plate must of course be transparent to the wavelengths emitted by the light sources, since during operation said wavelengths need to radiate through both the sealing plate and the coupled window.

In a preferred embodiment, the sealing plate is temperature controllable in order to avoid drops of condensation at the interface between the window and the sealing plate. Preferably, the temperature is adjusted to about 5 to 15 degrees above the intended temperature in the reaction vessel. The temperature adjustment sets not only the temperature of the sealing plate but also, in the case of a thermally conducting coupling, the temperature of the window in the vessel outer wall. In this way, drops of dew which might falsify the foam detector result owing to their optical scattering can be reliably prevented.

As already mentioned at the outset, foam sensors are frequently used to control the use of foam-controlling means according to demand. In one embodiment of the present invention, therefore, the illumination and detection unit has further assigned to it a control unit which is set up such that the at least one first light source, the at least one second light source and the at least one photodetector and also a metering pump which conveys antifoaming agents into the bioreactor vessel are controlled as a function of the latest detection status of the foam sensor. Said control unit is preferably arranged with the illumination and detection unit in a common housing. This measure serves the goal of modularity that has already been addressed above. The entire sensor and control electronics for the sensor and the associated foam-controlling means are thus combined in one easy-to-handle, reusable module which has no contact with the vessel interior and is therefore not subject to high sterilization requirements.

The control unit is favorably set up to control measuring cycles and cleaning cycles alternatingly, wherein, during the measuring cycles, the at least one first light source emits visible light and a reflection signal generated by the at least one photodetector is evaluated and wherein, during the cleaning cycles, the at least one second light source emits ultraviolet light. In other words, there is an alternation between measuring and cleaning. The measurement principle behind the optical sensor has already been explained above. If the sensor does not detect any foam in a measuring cycle, the next measuring cycle can immediately follow. However, if the detector detects foam in a measuring cycle, a cleaning cycle in which the photocatalytic coating of the window is activated by UV irradiation by means of the second light source is preferably carried out prior to the next measuring cycle. This thus ensures that if antifoaming measures initiated owing to a preceding measured result were successful, this is also determined in the next measuring cycle and not for instance concealed by still adherent foam residues. In another embodiment, measuring and cleaning cycles are controlled strictly alternatingly independently of the detection result.

To further increase the reliability of the measured result, the illumination and detection unit preferably comprises a plurality of photodetectors which are orientated differently and which are assigned to different segments of the window. Multiple measurements are thus carried out at the same time for different window regions and can be compared to one another by the control unit. For example, a measured result which determines "foam" for a higher-positioned window region and determines "no foam" for a lower-positioned window region is indicative of adherent foam residues in the upper window region. By means of multiple photodetectors, it is also possible to obtain a quantitative measurement which indicates the foam level, instead of the purely qualitative result of "foam" or "no foam".

To improve foam detection, it can be further envisioned that, during the measuring cycles, the at least one first light source emits in a temporally modulated manner and the reflection signal of the at least one photodetector is preprocessed by means of a lock-in amplifier clocked with the modulation of the at least one first light source. The form of the modulation is preferably sinusoidal. The modulation frequency is preferably in the range from a few hundred hertz up to a few kilohertz. The lock-in principle, which is known in principle, makes it possible for components of the detection signal which do not correspond to the modulation frequency of the light source and which, for example, can originate from ambient illumination, to be reliably distinguished from the light used for foam detection.

Further features and advantages of the invention will be apparent from the following, specific description and from the drawing.

DETAILED DESCRIPTION OF PREFERRED EMBODIMENTS

Figure 1:
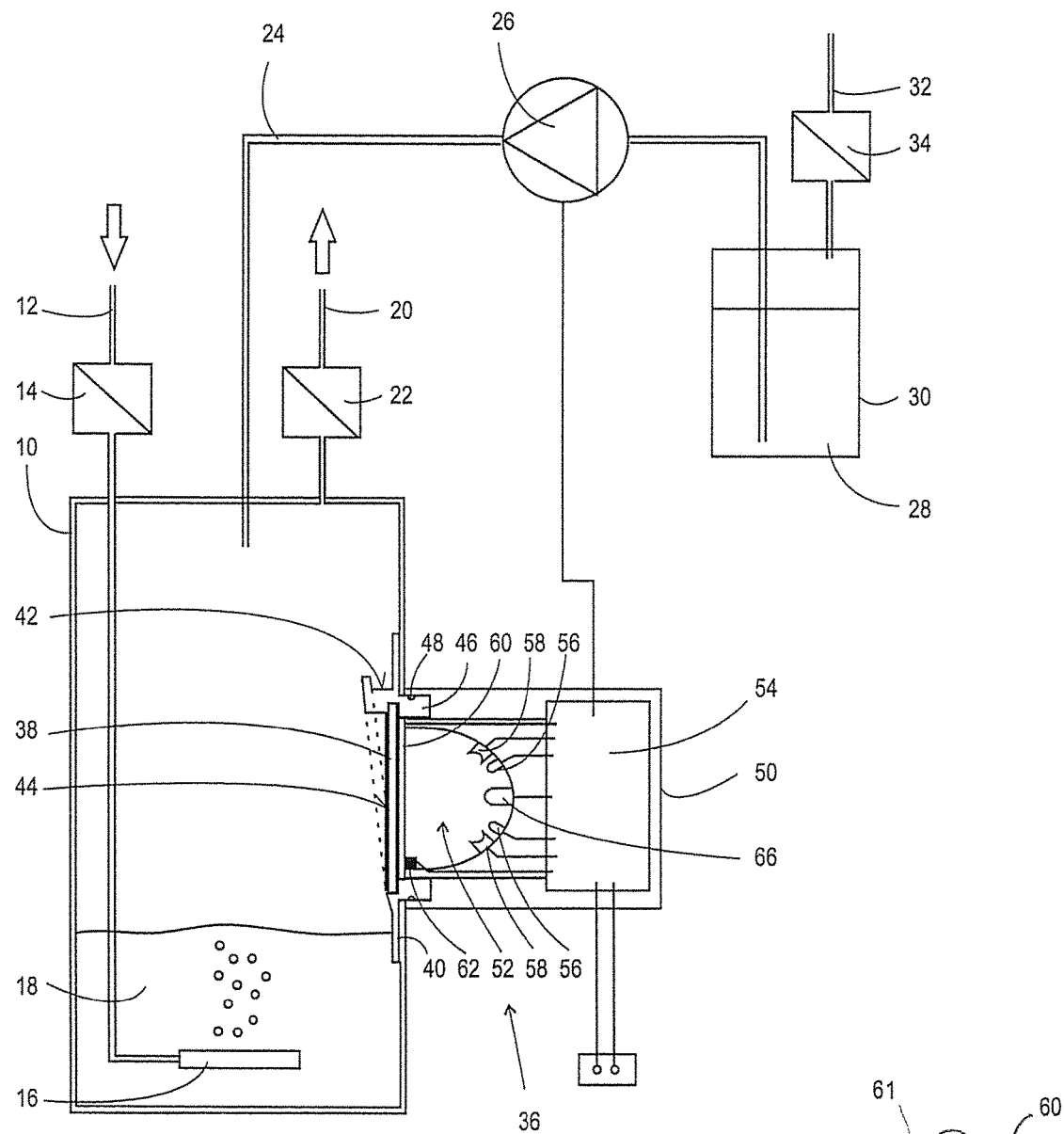
FIG. 1 a diagram showing a preferred embodiment of the bioreactor vessel according to the invention.
Figure 1A:
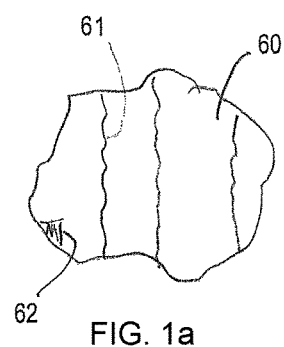
FIG. 1a is an elevational view of a portion of the sealing plate of the illumination and detection unit.

FIG. 1 shows a diagram of a preferred embodiment of a bioreactor vessel 10 according to the invention. The vessel 10 preferably comprises flexible wall material, preferably composed of plastic, and is particularly preferably in the form of a bag. Gas can be introduced into the vessel interior via a flexible supply line 12, and a sterile filter 14 is preferably arranged in the supply line 12. In the embodiment shown in FIG. 1, gas is introduced via a sparger 16, which distributes the supplied gas as bubbles in a liquid medium 18 in the interior of the vessel 10. Gas can be removed from the vessel 10 via a discharge line 20, in which a sterile filter 22 is likewise preferably arranged.

In order for it to be possible to specifically counteract foam development, as occurs in many biological reactions, the vessel 10 comprises an additional supply line for antifoaming agents (AFAs), called AFA supply line 24 here for short. The AFA supply line is connected to a metering pump 26, which is able to pump antifoaming agents 28 from a storage vessel into the vessel 10 via the AFA supply line 24. In the embodiment shown, the AFA storage vessel 30 is charged via its own supply line 32 having a sterile filter 34.

A particular foam sensor 36 is provided for control of the metering pump 26. The foam sensor 36 comprises disposable elements which are connected securely to the disposable vessel 10 and together therewith can be sterilized and disposed of after use. At the same time, the foam sensor 36 comprises reusable elements which, in the preferred embodiment, do not require any sterilization, since at no point do they come into contact with the interior of the vessel 10.

Securely connected to the wall of the vessel 10 is a window 38 which is at least transparent to visible and ultraviolet light. Window material which can be used includes both plastics such as, for example, PC, PET, PMAA, etc. and glasses, for example float glass, quartz, sapphire, etc. In the embodiment shown, the window 38 is connected to a plastics frame 40 in a secure and gas- and liquid-tight manner, and the plastics frame 40 is connected, more particularly welded or adhesively bonded, to the wall of the vessel 10 in a secure and gas- and liquid-tight manner. Above the window, the frame 40 has a collection and drainage channel 42 for condensate which has accumulated on the wall of the vessel 10 above the frame 40. This thus prevents the condensate from running over the window and possibly impairing sensor operation.

The inner side of the window comprises a coating 44 composed of photocatalytically active titanium dioxide, especially with an anatase crystal structure. Nanocrystalline coatings of this kind are transparent to visible light and can be readily applied to the abovementioned preferred window materials.

In the embodiment shown in FIG. 1, a flange 46 of the frame 40 penetrates the wall of the vessel 10. This flange is provided with a locking device 48. Alternatively, a thread or another, preferably reversible, fastening device could also be provided on the flange 46. Said fastening device is used to couple a detector housing 50.

The detector housing 50 comprises all the essential elements for foam detection and for appropriate control of the metering pump 26. The elements contained in the detector housing can be roughly divided according to their function into the illumination and detection unit 52 and the control unit 54. In the present case, the illumination and detection unit 52 comprises multiple LEDs 56 for visible light and multiple photodetectors 58 for detection of the same spectral range. The light of the LEDs 56 radiates through the window 38 and is, if present, reflected by foam in the interior space of the vessel 10. The reflected light falls back through the window 38 onto the photodetectors 56. The resulting reflection signal, i.e. the electrical output signal of the photodetectors 58, is conducted to the control unit 54, which also controls the LEDs 56. More particularly, control is preferably effected in modulated form. The modulation frequency of the LEDs 56, which is in the range from a few hundred hertz up to a few kilohertz, is fed as a clock signal to a lock-in amplifier contained in the control unit 54, which preamplifies the reflection signal of the photodetectors 58. The principle behind the lock-in amplifier is well known to a person skilled in the art.

Depending on the strength of the reflection signal, the control unit 54 can distinguish whether foam is situated in front of the window 38 or not. Choosing a suitable threshold is the result of a calibration which has to be carried out in each individual case.

In principle, it is possible to evaluate the multiple photodetectors 58 together and redundantly. However, it may be more favorable to orientate the photodetectors 58, as shown in FIG. 1, differently and more particularly to different regions of the window 38 and to evaluate their signals separately. As a result, the foam conditions in front of different regions of the window 38 can be evaluated separately, making it possible for example to determine the foam level.

The illumination and detection unit is sealed with respect to the window 38 by a sealing plate 60, which is here likewise transparent to visible and UV light. The electronics accommodated in the housing 50 are thus protected from soiling and damage. The sealing plate 60 is preferably arranged such that, upon coupling of the detector housing 50 to the vessel 10, it is directly in contact with the outer side of the window 38. However, this will not always be perfectly possible. Therefore, it has to be expected that water of condensation will collect in the space between the window 38 and the sealing plate 40, and this might interfere with foam detection. In the embodiment shown in FIG. 1, a heating device 61 is therefore provided, for example in the form of electric heating wires on the sealing plate 60. Said heating device 61 is likewise controlled by the control unit 54. It receives information concerning the plate temperature from a temperature sensor 62 and preferably information concerning the temperature in the reactor vessel 10 from a further temperature sensor not shown in the FIGURE. Preferably, in order to prevent water of condensation, the plate temperature is adjusted to about 5 to 15, more particularly to about 10 degrees above the temperature in the reactor vessel 10.

The metering pump 26 is controlled by the control device 54 via the control line 64 according to the result from the foam detection.

A further element comprised by the illumination and detection unit is a UV light source, preferably a UV LED 66, which is likewise controlled by the control unit 54. The spectral range of the emission of the UV LED 66 comprises light having a wavelength suitable for activating the photocatalytic coating 44 of the window 38. This means that typically light components having a wavelength less than 390 nanometers must be present. This applies in particular to an anatase coating, whose band gaps correspond energetically approximately to a wavelength of 387 nanometers. In the case of a coating substantially containing rutile crystals, the band gaps are slightly narrower and correspond energetically to a wavelength of about 412 nanometers. However, it has been found that anatase coatings are more effective.

In a preferred method for controlling the foam detector 36, the foam detection measurement is carried out in cycles, wherein a measuring cycle is between 0.5 and 5 seconds, more particularly about 1 second. Following the measuring cycle, a cleaning cycle can take place, in which the UV LED 66 irradiates the coating 44 for about 1 to 10 seconds, more particularly for about 5 seconds, and thus activates it.

Thereafter, a new measuring cycle can take place. Alternatively, it is also possible to carry out the cleaning cycle only, or at least especially, when the result of the preceding measuring cycle indicates foam in front of the window 38. In these cases, soiling of the window and the need for cleaning has to be expected. However, the cleaning cycle must be carried out at least every now and again, even if no foam has been detected in front of the window, since the superhydrophilicity of the window 38 generated by UV irradiation decays in the absence of UV irradiation. This fosters the risk of drops of dew which would interfere with a subsequent measurement.

It will be appreciated that the embodiments discussed in the specific description and shown in the FIGURE are only illustrative exemplary embodiments of the present invention. In light of the disclosure here, a broad spectrum of possible variations is available to a person skilled in the art. More particularly, the number of foam detectors 36 in the reactor vessel 10 is freely selectable and can be adapted to particular requirements. The number and arrangement of the light sources and photodetectors in the illumination and detection unit 52 can also be adapted by a person skilled in the art to the requirements of the individual case.

The invention claimed is:

1. A bioreactor comprising:
   a vessel having a flexible outer wall for containing fluids, the flexible outer wall having an inner surface facing into the vessel;
   a supply of antifoaming agent communicating with the vessel;
   a metering pump for selectively conveying the antifoaming agent to the vessel;
   at least one window mounted to a frame, the frame being welded or bonded to the inner surface of the flexible outer wall of the vessel and having a flange penetrating through the flexible outer wall of the vessel at a position in said outer wall of the vessel so that the window is above the fluids contained in the vessel, said window comprising an outer side and an inner side and being transparent to light from the visible and ultraviolet spectral range;
   an illumination and detection unit having a housing reversibly coupled to the flange that penetrates through the flexible outer wall of said vessel, the illumination and detection unit further comprising at least one first light source of visible light disposed in the housing to direct light through the window and into the vessel, at least one photodetector in the housing and external of the vessel and disposed to detect reflected light from said first light source that is reflected in the vessel and to generate a reflection signal;
   a control unit connected to the photodetector and to the metering pump and operative to actuate the metering pump for conveying the antifoaming agent into the vessel when the reflection signal generated by the photodetector exceeds a threshold value indicative of a specified level of foaming in the vessel and
   the illumination and detection unit further comprises a coupling surface comprising a sealing plate that is transparent to light from the visible and ultraviolet spectral range, and the sealing plate including an electric heating device that is temperature controllable.

2. The bioreactor of claim 1, characterized in that the control unit controls the illumination and detection unit for performing measuring cycles during which first light source directs light through the window and into the vessel and the photodetector detects reflected light from said first light source, and cleaning cycles alternating with the measuring cycles when the reflection signal generated by the photodetector exceeds the threshold value.

3. The bioreactor of claim 2, characterized in that, during the measuring cycles, the at least one first light source emits light in a temporally modulated manner, the at least one photodetector detects light from said at least one first light source that is reflected in the vessel and sends the reflection signal to said control unit and the reflection signal of the at least one photodetector is preprocessed by a lock-in amplifier clocked with the modulation of the at least one first light source.

4. The bioreactor of claim 1, wherein the inner side of the window is provided with a coating of a photocatalytically active material that is transparent to visible light and is a activated by ultraviolet light.

5. The bioreactor of claim 4, further comprising at least one second light source of ultraviolet light for activating the photocatalytically active material on the inner side of the window.

6. The bioreactor of claim 1, wherein the frame includes a collection and drainage channel extending along an upper surface of the frame and adjacent the inner surface of the flexible outer wall of the vessel for drainage condensate and preventing the condensate from running over the window.

7. The bioreactor of claim 1, wherein the control unit is in the housing.

* * * * *